(12) United States Patent
Payen

(10) Patent No.: US 12,209,236 B2
(45) Date of Patent: Jan. 28, 2025

(54) OVEREXPRESSION OF FUMARATE REDUCTASE RESULTS IN AN INCREASED FERMENTATION RATE IN YEAST

(71) Applicant: DANISCO US INC., Palo Alto, CA (US)

(72) Inventor: Celia Emily Gaby Payen, Wilmington, DE (US)

(73) Assignee: DANISCO US INC., Palo Alto, CA (US)

( * ) Notice: Subject to any disclaimer, the term of this patent is extended or adjusted under 35 U.S.C. 154(b) by 1101 days.

(21) Appl. No.: 17/058,612

(22) PCT Filed: May 24, 2019

(86) PCT No.: PCT/US2019/033880
§ 371 (c)(1),
(2) Date: May 27, 2021

(87) PCT Pub. No.: WO2019/226972
PCT Pub. Date: Nov. 28, 2019

(65) Prior Publication Data
US 2021/0207076 A1     Jul. 8, 2021

Related U.S. Application Data

(60) Provisional application No. 62/676,446, filed on May 25, 2018.

(51) Int. Cl.
| C12N 1/16 | (2006.01) |
| C12N 9/02 | (2006.01) |
| C12N 15/52 | (2006.01) |
| C12P 1/02 | (2006.01) |
| C12P 7/06 | (2006.01) |

(52) U.S. Cl.
CPC .............. *C12N 1/16* (2013.01); *C12N 9/001* (2013.01); *C12N 15/52* (2013.01); *C12P 1/02* (2013.01); *C12P 7/06* (2013.01); *C12Y 103/01006* (2013.01)

(58) Field of Classification Search
CPC .......... C12N 1/16; C12N 9/001; C12N 15/52; C12P 1/02; C12P 7/06; C12Y 103/01006; Y02E 50/10
See application file for complete search history.

(56) References Cited

U.S. PATENT DOCUMENTS

| 9,689,005 B2 * | 6/2017 | Verwaal ................. C12N 15/81 |
| 10,428,354 B2 * | 10/2019 | Miasnikov ........... C12N 9/1029 |
| 2004/0186070 A1 | 9/2004 | Penttila et al. |

FOREIGN PATENT DOCUMENTS

| WO | 2014/018755 A1 | 1/2014 |
| WO | 2015/148272 A1 | 10/2015 |

OTHER PUBLICATIONS

Salusjärvi et al. 2013, "Overexpression of NADH-dependent fumarate reductase improves d-xylose fermentation in recombinant *Saccharomyces cerevisiae*", J Ind Microbiol Biotechnol. 40:1383-1392; DOI 10.1007/s10295-013-1344-9 (Year: 2013).*

Muratsubaki and Enomoto, 1998, "One of the Fumarate Reductase Isoenzymes from *Saccharomyces cerevisiae* Is Encoded by the OSM1 Gene", Archives of Biochemistry and Biophysics. vol. 352, No. 2, Apr. 15, pp. 175-181. Article No. BB980583 (Year: 1998).*

Zhang et al. 2015. "Substrate and product inhibition on yeast performance in ethanol fermentation." Energy & Fuels, 29(2), pp. 1019-1027 (Year: 2015).*

Gasser, Brigitte et al., Engineering of Pichia pastoris for Improved Production of Antibody Fragments, Biotechnology and Bioengineering, Jun. 5, 2006, pp. 353-361, vol. 94, No. 2.

Salusjärvi, Laura et al., Overexpression of NADH-dependent fumarate reductase improves d-xylose fermentation in recombinant *Saccharomyces cerevisiae*, J Ind Microbiol Biotechnol, 2013, pp. 1383-1392; No. 40.

Valkonen, Mari et al., Effects of Inactivation and Constitutive Expression of the Unfolded-Protein Response Pathway on Protein Production in the Yeast *Saccharomyces cerevisiae*, Applied and Environmental Microbiology, Apr. 2003, p. 2065-2072, vol. 69, No. 4.

International Search Report and Written Opinion—PCT/US2019/033880—mailed Jul. 7, 2019.

* cited by examiner

*Primary Examiner* — Aaron J Kosar
*Assistant Examiner* — Andrew T Moehlman

(57) ABSTRACT

Described are compositions and methods relating to modified yeast that overexpress fumarate reductase. The yeast cells have an increased fermentation rate compared to their parental cells. Such yeast cells ae particularly useful for large-scale ethanol production from starch substrates where an increased rate of ethanol production is desirable.

19 Claims, No Drawings
Specification includes a Sequence Listing.

SEQUENCE LISTING

<160> NUMBER OF SEQ ID NOS: 4

<210> SEQ ID NO 1
<211> LENGTH: 1506
<212> TYPE: DNA
<213> ORGANISM: Saccharomyces cerevisiae

<400> SEQUENCE: 1

| | | | | | |
|---|---|---|---|---|---|
| atgattagat | ctgtgagaag | ggttttcatt | tacgtctcaa | tattcgtatt | gataatagtt | 60 |
| ttgaaaagaa | cattaagtgg | cacagatcaa | acgtcaatga | acaaccagt | ggtggtcatt | 120 |
| ggctctggtt | tggcaggctt | aaccacaagt | aatcgtctca | ttagtaaata | cagaattcct | 180 |
| gttgtgcttt | tggataaggc | ggcttctatt | ggtgggaact | ctataaaggc | ttctagtggt | 240 |
| attaatggtg | ctcacacaga | cactcaacaa | aatttaaagg | taatggacac | tcccgaattg | 300 |
| tttttgaaag | atactttgca | ttcggctaaa | ggcagagggg | ttccatcact | gatggataag | 360 |
| ttgactaagg | aatccaagag | tgctatcagg | tggttgcaaa | cagaattcga | tttgaaatta | 420 |
| gacctccttg | cgcaattggg | cggtcactct | gttccaagga | cccatagatc | ttctggcaaa | 480 |
| ttaccaccag | ttttgaaat | cgtgcaagcg | ttatcaaaaa | aactaaagga | tatctcttcc | 540 |
| aaagattcca | atctcgtgca | gattatgcta | aacagtgaag | tagtggatat | cgagcttgat | 600 |
| aatcaaggtc | atgttactgg | tgtagtatat | atggacgaga | acggaaaccg | taaaatcatg | 660 |
| aaatcacacc | atgtcgtgtt | ttgctcaggt | ggatttggtt | actctaagga | aatgttgaaa | 720 |
| gagtactcac | caaatttgat | tcacttgcca | actactaatg | gcaaacagac | tacaggtgat | 780 |
| ggtcaaaaaa | tcctttcaaa | gttgggtgcc | gaattgattg | atatggatca | agtgcaggta | 840 |
| caccctaccg | gcttcattga | tccaaatgac | cgtgaaaata | actggaagtt | tttggctgca | 900 |
| gaggcattga | ggggtttagg | cggcatctta | ttgcatccca | ccactggaag | aagatttaca | 960 |
| aatgaattga | gcaccagaga | tacagtaacc | atggaaatac | agtctaaatg | tccgaaaaat | 1020 |
| gataatagag | cacttttggt | aatgagcgac | aaagtctacg | agaactatac | gaataacata | 1080 |
| aactttata | tgtccaaaaa | cttaatcaaa | aaagtgtcaa | tcaacgatct | gatccgacaa | 1140 |
| tatgacctac | aaactacagc | ttctgaactg | gtgactgaac | tgaagagtta | ttccgatgtt | 1200 |
| aatactaagg | atacgtttga | taggccattg | attatcaatg | cctttgataa | agatatttcg | 1260 |
| actgaatcaa | ctgtttatgt | tggggaagtt | acaccagttg | ttcatttcac | aatgggtggt | 1320 |
| gtgaaaatta | atgagaaatc | tcaggtaatt | aagaaaaatt | cggaaagcgt | tctatctaat | 1380 |
| gggatatttg | ctgctggtga | agtttcgggt | ggtgttcatg | gagccaacag | attgggtgga | 1440 |
| tctagtttgt | tagagtgtgt | tgtctttgga | aagacagctg | cggataacat | agcaaaattg | 1500 |
| tactga | | | | | 1506 |

<210> SEQ ID NO 2
<211> LENGTH: 792
<212> TYPE: DNA
<213> ORGANISM: Artificial Sequence
<220> FEATURE:
<223> OTHER INFORMATION: Artificial promoter

<400> SEQUENCE: 2

| | | | | | |
|---|---|---|---|---|---|
| gcaacacacg | agtatgttgt | acctaaatca | ataccgacag | cttttgacat | attatctgtt | 60 |
| atttacttga | atttttgttt | cttgtaatac | ttgattactt | ttcttttgat | gtgcttatct | 120 |
| tacaaataga | gaaaataaaa | caacttaagt | aagaattggg | aaacgaaact | acaactcaat | 180 |
| cccttctcga | agatacatca | atccacccct | tatataacct | tgaagtcctc | gaaacgatca | 240 |
| gctaatctaa | atggcccccc | ttctttttgg | gttctttctc | tcccttttgc | cgccgatgga | 300 |
| acgttctgga | aaagaagaa | taatttaatt | actttctcaa | ctaaaatctg | gagaaaaaac | 360 |
| gcaaatgaca | gcttctaaac | gttccgtgtg | ctttctttct | agaatgttct | ggaaagttta | 420 |
| caacaatcca | caagaacgaa | aatgccgttg | acaatgatga | aaccatcatc | cacacaccgc | 480 |

```
gcacacgtgc tttatttctt tttctgaatt ttttttttcc gccatttca accaaggaaa      540 tttttttct  tagggctcag aacctgcagg tgaagaagcg ctttagaaat caaagcacaa      600
cgtaacaatt tgtcgacaac cgagcctttg aagaaaaaat ttttcacatt gtcgcctcta      660
aataaatagt ttaaggttat ctacccacta tatttagttg ttctttttt ttttccttct       720 actctttatc ttttacctc atgctttcta cctttcagca ctgaagagtc caaccgaata       780
tatacacaca ta                                                          792
```

```
<210> SEQ ID NO 3
<211> LENGTH: 501
<212> TYPE: PRT
<213> ORGANISM: Saccharomyces cerevisiae

<400> SEQUENCE: 3

Met Ile Arg Ser Val Arg Val Phe Ile Tyr Val Ser Ile Phe Val
1               5                   10                  15

Leu Ile Ile Val Leu Lys Arg Thr Leu Ser Gly Thr Asp Gln Thr Ser
                20                  25                  30

Met Lys Gln Pro Val Val Ile Gly Ser Gly Leu Ala Gly Leu Thr
            35                  40                  45

Thr Ser Asn Arg Leu Ile Ser Lys Tyr Arg Ile Pro Val Val Leu Leu
        50                  55                  60

Asp Lys Ala Ala Ser Ile Gly Gly Asn Ser Ile Lys Ala Ser Ser Gly
65                  70                  75                  80

Ile Asn Gly Ala His Thr Asp Thr Gln Gln Asn Leu Lys Val Met Asp
                85                  90                  95

Thr Pro Glu Leu Phe Leu Lys Asp Thr Leu His Ser Ala Lys Gly Arg
            100                 105                 110

Gly Val Pro Ser Leu Met Asp Lys Leu Thr Lys Glu Ser Lys Ser Ala
        115                 120                 125

Ile Arg Trp Leu Gln Thr Glu Phe Asp Leu Lys Leu Asp Leu Leu Ala
    130                 135                 140

Gln Leu Gly Gly His Ser Val Pro Arg Thr His Arg Ser Ser Gly Lys
145                 150                 155                 160

Leu Pro Pro Gly Phe Glu Ile Val Gln Ala Leu Ser Lys Lys Leu Lys
                165                 170                 175

Asp Ile Ser Ser Lys Asp Ser Asn Leu Val Gln Ile Met Leu Asn Ser
            180                 185                 190

Glu Val Val Asp Ile Glu Leu Asp Asn Gln Gly His Val Thr Gly Val
        195                 200                 205

Val Tyr Met Asp Glu Asn Gly Asn Arg Lys Ile Met Lys Ser His His
    210                 215                 220

Val Val Phe Cys Ser Gly Gly Phe Gly Tyr Ser Lys Glu Met Leu Lys
225                 230                 235                 240

Glu Tyr Ser Pro Asn Leu Ile His Leu Pro Thr Thr Asn Gly Lys Gln
                245                 250                 255

Thr Thr Gly Asp Gly Gln Lys Ile Leu Ser Lys Leu Gly Ala Glu Leu
            260                 265                 270

Ile Asp Met Asp Gln Val Gln His Pro Thr Gly Phe Ile Asp Pro
        275                 280                 285

Asn Asp Arg Glu Asn Asn Trp Lys Phe Leu Ala Ala Glu Ala Leu Arg
    290                 295                 300

Gly Leu Gly Gly Ile Leu Leu His Pro Thr Thr Gly Arg Arg Phe Thr
```

```
305                 310                 315                 320
Asn Glu Leu Ser Thr Arg Asp Thr Val Thr Met Glu Ile Gln Ser Lys
                325                 330                 335
Cys Pro Lys Asn Asp Asn Arg Ala Leu Leu Val Met Ser Asp Lys Val
                340                 345                 350
Tyr Glu Asn Tyr Thr Asn Asn Ile Asn Phe Tyr Met Ser Lys Asn Leu
                355                 360                 365
Ile Lys Lys Val Ser Ile Asn Asp Leu Ile Arg Gln Tyr Asp Leu Gln
                370                 375                 380
Thr Thr Ala Ser Glu Leu Val Thr Glu Leu Lys Ser Tyr Ser Asp Val
385                 390                 395                 400
Asn Thr Lys Asp Thr Phe Asp Arg Pro Leu Ile Ile Asn Ala Phe Asp
                405                 410                 415
Lys Asp Ile Ser Thr Glu Ser Thr Val Tyr Val Gly Glu Val Thr Pro
                420                 425                 430
Val Val His Phe Thr Met Gly Gly Val Lys Ile Asn Glu Lys Ser Gln
                435                 440                 445
Val Ile Lys Lys Asn Ser Glu Ser Val Leu Ser Asn Gly Ile Phe Ala
        450                 455                 460
Ala Gly Glu Val Ser Gly Gly Val His Gly Ala Asn Arg Leu Gly Gly
465                 470                 475                 480
Ser Ser Leu Leu Glu Cys Val Val Phe Gly Lys Thr Ala Ala Asp Asn
                485                 490                 495
Ile Ala Lys Leu Tyr
            500

<210> SEQ ID NO 4
<211> LENGTH: 20
<212> TYPE: DNA
<213> ORGANISM: Artificial Sequence
<220> FEATURE:
<223> OTHER INFORMATION: Artificial guide RNA sequence

<400> SEQUENCE: 4
agtctcgaga atggcaagca                                              20
```

OVEREXPRESSION OF FUMARATE REDUCTASE RESULTS IN AN INCREASED FERMENTATION RATE IN YEAST

TECHNICAL FIELD

The present compositions and methods relate to modified yeast cells that over-expresses fumarate reductase. The yeast cells have an increased fermentation rate compared to their parental cells. Such yeast is particularly useful for large-scale ethanol production from starch substrates where an increased rate of ethanol production is desirable.

INCORPORATION BY REFERENCE OF THE SEQUENCE LISTING

The present application is being filed with a Sequence Listing in electronic format. The Sequence Listing is provided as a file entitled NB41489WOPCT_SeqListing.txt, created on May 14, 2019, which is 8,106 bytes in size. The information in the electronic format of the Sequence Listing is incorporated by reference in its entirety.

BACKGROUND

Yeast-based ethanol production is based on the conversion of sugars into ethanol. The current annual fuel ethanol production by this method is about 90 billion liters worldwide. It is estimated that about 70% of the cost of ethanol production is the feedstock. Since the ethanol production volume is so large, even small yield improvements have massive economic impact for the industry. The conversion of one mole of glucose into two moles of ethanol and two moles of carbon dioxide is redox-neutral, with the maximum theoretical yield being about 51%. The current industrial yield is about 45%; therefore, there are opportunities to increase ethanol production. Despite advances in yeast productivity, the need exists to further modify yeast metabolic pathways to maximize ethanol production, while not increasing the production of undesirable by-products.

SUMMARY

The present compositions and methods relate to modified yeast cells that over-expresses fumarate reductase. The yeast cells have an increased fermentation rate compared to their parental cells, thereby producing a similar maximum level of ethanol in a shorter period of time. Aspects and embodiments of the compositions and methods are described in the following, independently-numbered, paragraphs.

1. In one aspect, a method for increasing the rate of ethanol production in yeast cells grown on a carbohydrate substrate is provided, comprising: introducing into parental yeast cells a genetic alteration that causes the modified cells to produce an increased amount of fumarate reductase compared to the parental cells, wherein the modified cells have an increased rate of fermentation compared to the rate of fermentation of the parental cells under equivalent fermentation conditions.

2. In some embodiments of the method of paragraph 1, the genetic alteration comprises introduction into the parental cells of a nucleic acid capable of directing the expression of fumarate reductase to a level greater that of the parental cell grown under equivalent conditions.

3. In some embodiments of the method of paragraph 1, the genetic alteration comprises introduction of an expression cassette for expressing a fumarate reductase.

4. In some embodiments of the method of any of the preceding paragraphs, the fumarate reductase is a long or short form.

5. In some embodiments of the method of paragraph 4, the fumarate reductase is the short form.

6. In some embodiments of the method of any of the preceding paragraphs, ethanol production is measured at 24 hours into fermentation.

7. In some embodiments of the method of any of the preceding paragraphs, the increased rate of ethanol production is not due to the metabolism of xylose.

8. In some embodiments of the method of any of the preceding paragraphs, the carbohydrate substrate is substantially free of xylose.

9. In some embodiments of the method of any of the preceding paragraphs, the cells further comprise one or more genes of the phosphoketolase pathway.

10. In some embodiments of the method of paragraph 9, the genes of the phosphoketolase pathway are selected from the group consisting of phosphoketolase, phosphotransacetylase and acetylating acetyl dehydrogenase.

11. In some embodiments of the method of any of the preceding paragraphs, the amount of increase in the expression of fumarate reductase is about 80-fold compared to the level of expression in parental cells grown under equivalent conditions, based on OSM1 mRNA expression.

12. In some embodiments of the method of any of the preceding paragraphs, the cells further comprise an exogenous gene encoding a carbohydrate processing enzyme.

13. In some embodiments of the method of any of the preceding paragraphs, the cells further comprise an alteration in the glycerol pathway and/or the acetyl-CoA pathway.

14. In some embodiments of the method of any of the preceding paragraphs, the cells further comprise an alternative pathway for making ethanol.

15. In some embodiments of the method of wherein the cells further comprise, the cells are of a Saccharomyces spp.

These and other aspects and embodiments of present modified cells and methods will be apparent from the description, including the Drawings/Figures.

DETAILED DESCRIPTION

I. Definitions

Prior to describing the present yeast and methods in detail, the following terms are defined for clarity. Terms not defined should be accorded their ordinary meanings as used in the relevant art.

As used herein, the term "alcohol" refers to an organic compound in which a hydroxyl functional group (—OH) is bound to a saturated carbon atom.

As used herein, the terms "yeast cells," "yeast strains," or simply "yeast" refer to organisms from the phyla Ascomycota and Basidiomycota. Exemplary yeast is budding yeast from the order Saccharomycesles. Particular examples of yeast are Saccharomyces spp., including but not limited to S. cerevisiae. Yeast include organisms used for the production of fuel alcohol as well as organisms used for the production of potable alcohol, including specialty and proprietary yeast strains used to make distinctive-tasting beers, wines, and other fermented beverages.

As used herein, the phrase "engineered yeast cells," "variant yeast cells," "modified yeast cells," or similar phrases, refer to yeast that include genetic modifications and characteristics described herein. Variant/modified yeast do not include naturally occurring yeast.

As used herein, the terms "polypeptide" and "protein" (and their respective plural forms) are used interchangeably to refer to polymers of any length comprising amino acid residues linked by peptide bonds. The conventional one-letter or three-letter codes for amino acid residues are used herein and all sequence are presented from an N-terminal to C-terminal direction. The polymer can comprise modified amino acids, and it can be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art.

As used herein, functionally and/or structurally similar proteins are considered to be "related proteins," or "homologs." Such proteins can be derived from organisms of different genera and/or species, or different classes of organisms (e.g., bacteria and fungi), or artificially designed. Related proteins also encompass homologs determined by primary sequence analysis, determined by secondary or tertiary structure analysis, or determined by immunological cross-reactivity, or determined by their functions.

As used herein, the term "homologous protein" refers to a protein that has similar activity and/or structure to a reference protein. It is not intended that homologs necessarily be evolutionarily related. Thus, it is intended that the term encompass the same, similar, or corresponding enzyme(s) (i.e., in terms of structure and function) obtained from different organisms. In some embodiments, it is desirable to identify a homolog that has a quaternary, tertiary and/or primary structure similar to the reference protein. In some embodiments, homologous proteins induce similar immunological response(s) as a reference protein. In some embodiments, homologous proteins are engineered to produce enzymes with desired activity (ies).

The degree of homology between sequences can be determined using any suitable method known in the art (see, e.g., Smith and Waterman (1981) *Adv. Appl. Math.* 2:482; Needleman and Wunsch (1970) *J. Mol. Biol.,* 48:443; Pearson and Lipman (1988) *Proc. Natl. Acad. Sci. USA* 85:2444; programs such as GAP, BESTFIT, FASTA, and TFASTA in the Wisconsin Genetics Software Package (Genetics Computer Group, Madison, WI); and Devereux et al. (1984) *Nucleic Acids Res.* 12:387-95).

For example, PILEUP is a useful program to determine sequence homology levels. PILEUP creates a multiple sequence alignment from a group of related sequences using progressive, pair-wise alignments. It can also plot a tree showing the clustering relationships used to create the alignment. PILEUP uses a simplification of the progressive alignment method of Feng and Doolittle, (Feng and Doolittle (1987) *J. Mol. Evol.* 35:351-60). The method is similar to that described by Higgins and Sharp ((1989) CABIOS 5:151-53). Useful PILEUP parameters including a default gap weight of 3.00, a default gap length weight of 0.10, and weighted end gaps. Another example of a useful algorithm is the BLAST algorithm, described by Altschul et al. ((1990) *J. Mol. Biol.* 215:403-10) and Karlin et al. ((1993) *Proc. Natl. Acad. Sci. USA* 90:5873-87). One particularly useful BLAST program is the WU-BLAST-2 program (see, e.g., Altschul et al. (1996) *Meth. Enzymol.* 266:460-80). Parameters "W," "T," and "X" determine the sensitivity and speed of the alignment. The BLAST program uses as defaults a word-length (W) of 11, the BLOSUM62 scoring matrix (see, e.g., Henikoff and Henikoff (1989) *Proc. Natl. Acad. Sci. USA* 89:10915) alignments (B) of 50, expectation (E) of 10, M'5, N'-4, and a comparison of both strands.

As used herein, the phrases "substantially similar" and "substantially identical," in the context of at least two nucleic acids or polypeptides, typically means that a polynucleotide or polypeptide comprises a sequence that has at least about 70% identity, at least about 75% identity, at least about 80% identity, at least about 85% identity, at least about 90% identity, at least about 91% identity, at least about 92% identity, at least about 93% identity, at least about 94% identity, at least about 95% identity, at least about 96% identity, at least about 97% identity, at least about 98% identity, or even at least about 99% identity, or more, compared to the reference (i.e., wild-type) sequence. Percent sequence identity is calculated using CLUSTAL W algorithm with default parameters. See Thompson et al. (1994) *Nucleic Acids Res.* 22:4673-4680. Default parameters for the CLUSTAL W algorithm are:

Gap opening penalty: 10.0
Gap extension penalty: 0.05
Protein weight matrix: BLOSUM series
DNA weight matrix: IUB
Delay divergent sequences %: 40
Gap separation distance: 8
DNA transitions weight: 0.50
List hydrophilic residues: GPSNDQEKR
Use negative matrix: OFF
Toggle Residue specific penalties: ON
Toggle hydrophilic penalties: ON
Toggle end gap separation penalty OFF Another indication that two polypeptides are substantially identical is that the first polypeptide is immunologically cross-reactive with the second polypeptide. Typically, polypeptides that differ by conservative amino acid substitutions are immunologically cross-reactive. Thus, a polypeptide is substantially identical to a second polypeptide, for example, where the two peptides differ only by a conservative substitution. Another indication that two nucleic acid sequences are substantially identical is that the two molecules hybridize to each other under stringent conditions (e.g., within a range of medium to high stringency).

As used herein, the term "gene" is synonymous with the term "allele" in referring to a nucleic acid that encodes and directs the expression of a protein or RNA. Vegetative forms of filamentous fungi are generally haploid, therefore a single copy of a specified gene (i.e., a single allele) is sufficient to confer a specified phenotype. The term "allele" is generally preferred when an organism contains more than one similar genes, in which case each different similar gene is referred to as a distinct "allele."

As used herein, the term "expressing a polypeptide" and similar terms refers to the cellular process of producing a polypeptide using the translation machinery (e.g., ribosomes) of the cell.

As used herein, "over-expressing a polypeptide," "increasing the expression of a polypeptide," and similar terms, refer to expressing a polypeptide at higher-than-normal levels compared to those observed with parental or "wild-type cells that do not include a specified genetic modification. Overexpression may be described in terms of mRNA levels or polypeptide levels, as experimental conditions permit.

As used herein, an "expression cassette" refers to a DNA fragment that includes a promoter, and amino acid coding region and a terminator (i.e., promoter::amino acid coding region::terminator) and other nucleic acid sequence needed to allow the encoded polypeptide to be produced in a cell. Expression cassettes can be exogenous (i.e., introduced into a cell) or endogenous (i.e., extant in a cell).

As used herein, the terms "fused" and "fusion" with respect to two DNA fragments, such as a promoter and the coding region of a polypeptide refer to a physical linkage causing the two DNA fragments to become a single molecule.

As used herein, the terms "wild-type" and "native" are used interchangeably and refer to genes, proteins or strains found in nature, or that are not intentionally modified for the advantage of the presently described yeast.

As used herein, the term "protein of interest" refers to a polypeptide that is desired to be expressed in modified yeast. Such a protein can be an enzyme, a substrate-binding protein, a surface-active protein, a structural protein, a selectable marker, a signal transducer, a receptor, a transporter, a transcription factor, a translation factor, a co-factor, or the like, and can be expressed. The protein of interest is encoded by an endogenous gene or a heterologous gene (i.e., gene of interest") relative to the parental strain. The protein of interest can be expressed intracellularly or as a secreted protein.

As used herein, "disruption of a gene" refers broadly to any genetic or chemical manipulation, i.e., mutation, that substantially prevents a cell from producing a function gene product, e.g., a protein, in a host cell. Exemplary methods of disruption include complete or partial deletion of any portion of a gene, including a polypeptide-coding sequence, a promoter, an enhancer, or another regulatory element, or mutagenesis of the same, where mutagenesis encompasses substitutions, insertions, deletions, inversions, and combinations and variations, thereof, any of which mutations substantially prevent the production of a function gene product. A gene can also be disrupted using CRISPR, RNAi, antisense, or any other method that abolishes gene expression. A gene can be disrupted by deletion or genetic manipulation of non-adjacent control elements. As used herein, "deletion of a gene," refers to its removal from the genome of a host cell. Where a gene includes control elements (e.g., enhancer elements) that are not located immediately adjacent to the coding sequence of a gene, deletion of a gene refers to the deletion of the coding sequence, and optionally adjacent enhancer elements, including but not limited to, for example, promoter and/or terminator sequences, but does not require the deletion of non-adjacent control elements. Deletion of a gene also refers to the deletion a part of the coding sequence, or a part of promoter immediately or not immediately adjacent to the coding sequence, where there is no functional activity of the interested gene existed in the engineered cell.

As used herein, the terms "genetic manipulation" and "genetic alteration" are used interchangeably and refer to the alteration/change of a nucleic acid sequence. The alteration can include but is not limited to a substitution, deletion, insertion or chemical modification of at least one nucleic acid in the nucleic acid sequence.

As used herein, a "functional polypeptide/protein" is a protein that possesses an activity, such as an enzymatic activity, a binding activity, a surface-active property, a signal transducer, a receptor, a transporter, a transcription factor, a translation factor, a co-factor, or the like, and which has not been mutagenized, truncated, or otherwise modified to abolish or reduce that activity. Functional polypeptides can be thermostable or thermolabile, as specified.

As used herein, "a functional gene" is a gene capable of being used by cellular components to produce an active gene product, typically a protein. Functional genes are the antithesis of disrupted genes, which are modified such that they cannot be used by cellular components to produce an active gene product, or have a reduced ability to be used by cellular components to produce an active gene product.

As used herein, yeast cells have been "modified to prevent the production of a specified protein" if they have been genetically or chemically altered to prevent the production of a functional protein/polypeptide that exhibits an activity characteristic of the wild-type protein. Such modifications include, but are not limited to, deletion or disruption of the gene encoding the protein (as described, herein), modification of the gene such that the encoded polypeptide lacks the aforementioned activity, modification of the gene to affect post-translational processing or stability, and combinations, thereof.

As used herein, "attenuation of a pathway" or "attenuation of the flux through a pathway," i.e., a biochemical pathway, refers broadly to any genetic or chemical manipulation that reduces or completely stops the flux of biochemical substrates or intermediates through a metabolic pathway. Attenuation of a pathway may be achieved by a variety of well-known methods. Such methods include but are not limited to: complete or partial deletion of one or more genes, replacing wild-type alleles of these genes with mutant forms encoding enzymes with reduced catalytic activity or increased Km values, modifying the promoters or other regulatory elements that control the expression of one or more genes, engineering the enzymes or the mRNA encoding these enzymes for a decreased stability, misdirecting enzymes to cellular compartments where they are less likely to interact with substrate and intermediates, the use of interfering RNA, and the like.

As used herein, "aerobic fermentation" refers to growth in the presence of oxygen.

As used herein, "anaerobic fermentation" refers to growth in the absence of oxygen.

As used herein, the expression "end of fermentation" refers to the stage of fermentation when the economic advantage of continuing fermentation to produce a small amount of additional alcohol is exceeded by the cost of continuing fermentation in terms of fixed and variable costs. In a more general sense, "end of fermentation" refers to the point where a fermentation will no longer produce a significant amount of additional alcohol, i.e., no more than about 1% additional alcohol, or no more substrate left for further alcohol production.

As used, herein, a "glucoamylase unit (GAU)" is defined as the amount of glucoamylase required to produce 1 g of glucose per hour from soluble starch substrate (4% ds) under assay conditions of 60° C. and pH 4.2.

As used herein, a "spectrophotometric acid protease unit (SAPU)" is the amount of protease activity that liberates one micromole of tyrosine per minute from a casein substrate under standard assay conditions.

As used herein, a "soluble starch unit (SSU)" is based on the degree of hydrolysis of soluble potato starch substrate (4% DS) by an aliquot of a-amylase at pH 4.5, 50° C. The reducing sugar content is measured using the DNS method as described by Miller, G. L. ((1959) *Anal. Chem.* 31:426-28).

As used herein, the singular articles "a," "an" and "the" encompass the plural referents unless the context clearly dictates otherwise. All references cited herein are hereby incorporated by reference in their entirety. The following abbreviations/acronyms have the following meanings unless otherwise specified:

° C. degrees Centigrade
AA α-amylase
AADH acetaldehyde dehydrogenases
ADH alcohol dehydrogenase
bp base pairs
DNA deoxyribonucleic acid
ds or DS dry solids
EC enzyme commission
EtOH ethanol
g or gm gram
g/L grams per liter
GA glucoamylase
GAU glucoamylase unit
H₂O water
HPLC high performance liquid chromatography
hr or h hour
kg kilogram
M molar
mg milligram
min minute
mL or ml milliliter
mM millimolar
mRNA messenger RNA
N normal
nm nanometer
PCR polymerase chain reaction
PKL phosphoketolase
ppm parts per million
PTA phosphotransacetylase
SAPU spectrophotometric acid protease unit
SSU soluble starch unit
Δ relating to a deletion
μg microgram
μL and μl microliter
μM micromolar II. Overexpression of a Fumarate Reductase in Yeast Increases the Rate of Ethanol Production Described are modified yeast, and methods of starch processing involving modified yeast, that have a genetic alteration resulting in the production of increased amounts of fumarate reductase compared to corresponding (i.e., otherwise-identical) parental cells. Fumarate reductase (E.C. 1.3.1.6) catalyzes the reduction of fumarate to succinate and is required for the reoxidation of intracellular NADH under anaerobic conditions.

Applicants have discovered that yeast cells overexpressing fumarate reductase have reduced fermentation times resulting in an increased amount of ethanol at an earlier time following the initiation of fermentation of a starch substrate compared to otherwise-identical parental cells. While fumarate reductate has been shown to improve D-xylose fermentation in *Saccharomyces cerevisiae* (Salusjärvi, L. et al. (2013) *J. Ind. Microbiol. Biotechnol.* 40:1383-92), there have heretofore been no reports that fumarate reductase can increase the rate of ethanol production.

The exemplified fumarate reductase is from *S. cerevisiae* S288c (Genbank Accession No. NP_012585.1; SEQ ID NO: 3 (infra)). However, Genbank lists about 20 other fumarate reductase polypeptide sequences with about 99% amino acid sequence identity to SEQ ID NO: 3, followed by a large number of other similar polypeptides. Most, if not all, of these similar polypeptides are expected to produce similar results in yeast cells.

Notably, the fumarate reductase gene, OSM1, is transcribed into a mRNA having two unique translation initiation sites, producing two different forms of functional fumarate reductase enzyme, one localizing to the ER and the other localizing to the mitochondria. As detailed, herein, an increase in either form of fumarate reductase appears to result in an increased fermentation rate in yeast. While the form of the fumarate reductase does appear to be critical, overexpression of the short form may be preferred.

In particular embodiments of the present compositions and methods, the amino acid sequence of the fumarate reductase polypeptide that is over-expressed in modified yeast cells has at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or even at least about 99% identity, to SEQ ID NO: 3, or to the short-form, thereof, identified as the underlined portion in SEQ ID NO: 3 (infra).

The increase in the fermentation rate of the modified cells may be an increase of at least 1.0%, at least 1.5%, at least 2.0%, at least 2.5%, at least 3.0%, at least 3.5%, at least 4.0%, at least 4.5%, at least 5.0%, or more, compared to the fermentation rate of the parental cells grown under the same conditions, as measured at 24 hr into (i.e., following the initiation of) fermentation.

The increase in the amount of fumarate reductase produced by the modified cells may be an increase of at least 20%, at least 30%, at least 40%, at least 50%, at least 70%, at least 100%, at least 150%, at least 200%, at least 500%, at least 1,000%, or more, compared to the amount of fumarate reductase produced by parental cells grown under the same conditions. Alternatively, or additionally, the increase in the amount of fumarate reductase produced by the modified cells may be at least 10-fold, at least 20-fold, at least 30-fold, and even at least 50-fold, or more, compared to the amount of fumarate reductase produced by parental cells grown under the same conditions.

The increase in the strength of the promoter used to control expression of the fumarate reductase produced by the modified cells may be at least 10-fold, at least 20-fold, at least 30-fold, at least 40-fold, at least 60-fold, or even at least 80-fold, or more, compared to strength of the native promoter controlling fumarate reductase expression, based on the amount of mRNA produced.

It is understood that relative promoter strength is not an exact scalar value. It can strongly depend on culture medium, fermentation time, temperature and other conditions. Values obtained from RNAseq data collected over the time course of fermentation in industrial medium are the most preferred, however, experimental and/or literature data obtained under different cultivation may also be used for recombinant promoter selection.

Preferably, increased fumarate reductase expression is achieved by genetic manipulation using sequence-specific molecular biology techniques, as opposed to chemical mutagenesis, which is generally not targeted to specific nucleic acid sequences. However, chemical mutagenesis is not excluded as a method for making modified yeast cells.

In some embodiments, the present compositions and methods involve introducing into yeast cells a nucleic acid capable of directing the over-expression, or increased expression, of a fumarate reductase polypeptide. Particular methods include but are not limited to (i) introducing an exogenous expression cassette for producing the polypeptide into a host cell, optionally in addition to an endogenous expression cassette, (ii) substituting an exogenous expression cassette with an endogenous cassette that allows the production of an increased amount of the polypeptide, (iii) modifying the promoter of an endogenous expression cassette to increase expression, (iv) increase copy number of the same or different cassettes for over-expression of fumarate reductase polypeptides, and/or (v) modifying any aspect of the host cell to increase the half-life of the polypeptide in the host cell.

In some embodiments, the parental cell that is modified already includes an engineered pathway of interest, such as a PKL pathway to increases ethanol production, or any other pathway to increase alcohol production. In some embodiments, the parental cell that is modified already includes a gene of interest, such as a gene encoding a selectable marker, carbohydrate-processing enzyme, or other polypeptide. In some embodiments, a gene of introduced is subsequently introduced into the modified cells.

It should be understood that the increased rate of ethanol production observed by overexpressing fumarate reductase is not due to the metabolism of xylose. Xylose was not present in the fermentation media used, in the appended Examples. Thus, the increased fermentation rate was observed from a carbohydrate substrate that is substantially free of, or entirely lacking, xylose, and can in no way be attributed to the metabolism of xylose.

III. Modified Yeast Cells Overexpressing Fumarate Reductase and Harboring an Exogenous PKL Pathway Increased expression of fumarate reductase can be combined with expression of genes of the PKL pathway to further increase the production rate, and/or the maximum production levels, of ethanol in yeast cells.

Engineered yeast cells having a heterologous PKL pathway have been previously described in WO2015148272 (Miasnikov et al.). These cells express heterologous phosphoketolase (PKL), phosphotransacetylase (PTA) and acetylating acetyl dehydrogenase (AADH), optionally with other enzymes, to channel carbon flux away from the glycerol pathway and toward the synthesis of acetyl-CoA, which is then converted to ethanol. Such modified cells are capable of increased ethanol production in a fermentation process when compared to otherwise-identical parent yeast cells.

IV. Overexpressing of Fumarate Reductase in Combination with Other Mutations that Affect Ethanol Production or by-Products, Thereof In some embodiments, in addition to overexpressing fumarate reductase, optionally in combination with the presence of an exogenous PKL pathway, the present modified yeast cells include additional modifications that affect ethanol production, or by products, thereof.

The modified cells may further include mutations that result in attenuation of the native glycerol biosynthesis pathway and/or reuse glycerol pathway, which are known to increase alcohol production. Methods for attenuation of the glycerol biosynthesis pathway in yeast are known and include reduction or elimination of endogenous NAD-dependent glycerol 3-phosphate dehydrogenase (GPD) or glycerol phosphate phosphatase activity (GPP), for example by disruption of one or more of the genes GPD1, GPD2, GPP1 and/or GPP2. See, e.g., U.S. Pat. No. 9,175,270 (Elke et al.), U.S. Pat. No. 8,795,998 (Pronk et al.) and U.S. Pat. No. 8,956,851 (Argyros et al.). Methods to enhance the reuse glycerol pathway by over expression of glycerol dehydrogenase (GCY1) and dihydroxyacetone kinase (DAK1) to convert glycerol to dihydroxyacetone phosphate (Zhang et al. (2013) *J. Ind. Microbiol. Biotechnol.* 40:1153-1160).

The modified yeast may further feature increased acetyl-CoA synthase (also referred to as acetyl-CoA ligase) activity (EC 6.2.1.1) to scavenge (i.e., capture) acetate produced by chemical or enzymatic hydrolysis of acetyl-phosphate (or present in the culture medium of the yeast for any other reason) and converts it to Ac-COA. This partially reduces the undesirable effect of acetate on the growth of yeast cells and may further contribute to an improvement in alcohol yield. Increasing acetyl-CoA synthase activity may be accomplished by introducing a heterologous acetyl-CoA synthase gene into cells, increasing the expression of an endogenous acetyl-CoA synthase gene and the like.

In some embodiments the modified cells may further include a heterologous gene encoding a protein with $NAD^+$-dependent acetylating acetaldehyde dehydrogenase (AADH) activity and/or a heterologous gene encoding a pyruvate formate lyase (PFL). The introduction of such genes in combination with attenuation of the glycerol pathway is described, e.g., in U.S. Pat. No. 8,795,998 (Pronk et al.). In some embodiments of the present compositions and methods the yeast expressly lacks a heterologous gene(s) encoding an acetylating acetaldehyde dehydrogenase, a pyruvate formate lyase or both.

In some embodiments, the present modified yeast cells may further overexpress a sugar transporter-like (STL1) polypeptide to increase the uptake of glycerol (see, e.g., Ferreira et al. (2005) *Mol Biol Cell* 16:2068-76; Dušková et al. (2015) *Mol Microbiol* 97:541-59 and WO 2015023989 A1).

In some embodiments, the present modified yeast cells further include a butanol biosynthetic pathway. In some embodiments, the butanol biosynthetic pathway is an isobutanol biosynthetic pathway. In some embodiments, the isobutanol biosynthetic pathway comprises a polynucleotide encoding a polypeptide that catalyzes a substrate to product conversion selected from the group consisting of: (a) pyruvate to acetolactate; (b) acetolactate to 2,3-dihydroxyisovalerate; (c) 2,3-dihydroxyisovalerate to 2-ketoisovalerate; (d) 2-ketoisovalerate to isobutyraldehyde; and (e) isobutyraldehyde to isobutanol. In some embodiments, the isobutanol biosynthetic pathway comprises polynucleotides encoding polypeptides having acetolactate synthase, keto acid reductoisomerase, dihydroxy acid dehydratase, ketoisovalerate decarboxylase, and alcohol dehydrogenase activity.

In some embodiments, the modified yeast cells comprising a butanol biosynthetic pathway further comprise a modification in a polynucleotide encoding a polypeptide having pyruvate decarboxylase activity. In some embodiments, the yeast cells comprise a deletion, mutation, and/or substitution in an endogenous polynucleotide encoding a polypeptide having pyruvate decarboxylase activity. In some embodiments, the polypeptide having pyruvate decarboxylase activity is selected from the group consisting of: PDC1, PDC5, PDC6, and combinations thereof. In some embodiments, the yeast cells further comprise a deletion, mutation, and/or substitution in one or more endogenous polynucleotides encoding FRA2, ALD6, ADH1, GPD2, BDH1, and YMR226C.

V. Fumarate Reductase Overexpression in Combination with Other Beneficial Mutations In some embodiments, in addition to overexpression of fumarate reductase, optionally in combination with other genetic modifications that benefit alcohol production, or reduction of byproducts, the present modified yeast cells further include any number of additional genes of interest encoding proteins of interest. Additional genes of interest may be introduced before, during, or after genetic manipulations that result in the overexpression of fumarate reductase polypeptides. Proteins of interest, include selectable markers, carbohydrate-processing enzymes, and other commercially-relevant polypeptides, including but not limited to an enzyme selected from the group consisting of a dehydrogenase, a transketolase, a phosphoketolase, a transladolase, an epimerase, a phytase, a xylanase, a β-glucanase, a phosphatase, a protease, an α-amylase, a β-amylase, a glucoamylase, a pullulanase, an isoamylase, a cellulase, a trehalase, a lipase, a pectinase, a polyesterase, a cutinase, an oxidase, a transferase, a reductase, a hemicellulase, a mannanase, an esterase, an isomerase, a pectinases, a lactase, a peroxidase and a laccase. Proteins of interest may be secreted, glycosylated, and otherwise-modified.

VI. Use of the Modified Yeast for Increased Alcohol Production

The present modified stains and methods of use, thereof, are not limited to a particular fermentation process. The present engineered yeast is expected to be a "drop-in" replacement for convention yeast in any alcohol fermentation facility, whether using raw starch hydrolysis, simultaneous saccharification and fermentation, or other standard variations of conventional ethanol production. While primarily intended for fuel alcohol production, the present yeast can also be used for the production of potable alcohol, including wine and beer.

VII. Yeast Cells Suitable for Modification

Yeasts are unicellular eukaryotic microorganisms classified as members of the fungus kingdom and include organisms from the phyla Ascomycota and Basidiomycota. Yeast that can be used for alcohol production include, but are not limited to, *Saccharomyces* spp., including *S. cerevisiae*, as well as *Kluyveromyces*, *Lachancea* and *Schizosaccharomyces* spp. Numerous yeast strains are commercially available, many of which have been selected or genetically engineered for desired characteristics, such as high alcohol production, rapid growth rate, and the like. Some yeast has been genetically engineered to produce heterologous enzymes, such as glucoamylase or α-amylase.

VII. Substrates and Products

Alcohol production from a number of carbohydrate substrates, including but not limited to corn starch, sugar cane, cassava, and molasses, is well known, as are innumerable variations and improvements to enzymatic and chemical conditions and mechanical processes. The present compositions and methods are believed to be fully compatible with such substrates and conditions.

Alcohol fermentation products include organic compound having a hydroxyl functional group (—OH) is bound to a carbon atom. Exemplary alcohols include but are not limited to methanol, ethanol, n-propanol, isopropanol, n-butanol, isobutanol, n-pentanol, 2-pentanol, isopentanol, and higher alcohols. The most commonly made fuel alcohols are ethanol, and butanol.

These and other aspects and embodiments of the present yeast strains and methods will be apparent to the skilled person in view of the present description.

EXAMPLES

The following examples are intended to further illustrate, but not limit, the described compositions and methods.

Example 1. Materials and Methods

The following protocols were employed unless otherwise specified.

Liquefact Preparation:

Liquefact (corn mash slurry) was prepared by adding 600 ppm of urea, 0.124 SAPU/g ds FERMGEN™ 2.5× (acid fungal protease), 0.33 GAU/g ds variant *Trichoderma reesei* glucoamylase, and 1.46 SSCU/g ds *Aspergillus kawachii* α-amylase, adjusted to a pH of 4.8.

Microtiter Plate Assays:

Factory liquefact (corn mash slurry) was subjected to centrifugation, and the supernatant filtered through 0.45 µm (sterilizing) filter. Clarified liquefact adjusted to dry solids content of 29% (corresponding to the dry solids content of crude liquefact of about 34%) was supplemented with 5 ml/L of a 10 mg/ml solution of ergosterol in TWEEN® 80 along with 600 mg/L urea, 0.124 SAPU/g ds acid fungal protease (i.e., FERMGEN™), 1.46 SSCU/g ds *Aspergillus kawachii* α-amylase, and stored frozen until used. 0.33 GAU/g ds variant of *Trichoderma reesei* glucoamylase was added immediately before the start of fermentation.

For fermentation assays, 800 µl of clarified liquefact were placed into each well of a deep 96-well MTP (Simport T110-10) and fermentation started with 10 µl of inoculum. The inocula were grown for ~24 h in SC6% synthetic medium containing yeast nitrogen base (0.67%), glucose (6%), and urea (0.2%), overnight. The deep well plates were closed with perforated ENZYSCREEN® lids. The lids were modified in such a way that the original rubber gasket was replaced with a (6-8 mm) slab of soft (Shore hardness 10) silicone rubber punctured with 26-gauge hypodermic needle over each of the 96 wells. This modification minimizes ethanol evaporation while allowing $CO_2$ to escape. Fermentation was conducted for up to 66 h at 32° C. with agitation.

HPLC Analysis:

At the end of fermentation, yeast was separated from the cultures by centrifugation (10 min at 3,900 rpm) and aliquots of the supernatant were filtered using Corning FILTREX™ CLS3505 96 well plates. The HPLC analysis was performed using PHENOMENEX REZEX™ RFQ Fast Acid H+ columns (a tandem of 50×7.8 mm and 100×7.8 mm) at 60° C. with a 0.6 ml/min isocratic flow rate in 5 mM $H_2SO_4$. An Agilent G1312A liquid chromatograph with refractive index detection was used. Unless otherwise noted, all values are reported in g/L.

Example 2. Over-Expression of OSM1 in Yeast

To overexpress the gene OSM1, which encodes both short and long forms of *Saccharomyces cerevisiae* fumarate reductase, two cassettes were constructed. The first cassette included the complete coding region of OSM1, and is referred to as OSM1-long or OSM1-L, and the second cassette started at codon-32 of OSM1, and is referred to as OSM1-short or OSM1-S.

The coding region of OSM1-L is represented, below, by SEQ ID NO: 1. The coding region of OSM1-S is represented by the underlined portion of SEQ ID NO: 1. The corresponding start codons are in bold.

(SEQ ID NO: 1)
ATGATTAGATCTGTGAGAAGGGTTTTCATTTACGTCTCAATATTCGTAT

TGATAATAGTTTTGAAAAGAACATTAAGTGGCACAGATCAAACGTCA<u>AT</u>

<u>GAAACAACCAGTGGTGGTCATTGGCTCTGGTTTGGCAGGCTTAACCACA</u>

<u>AGTAATCGTCTCATTAGTAAATACAGAATTCCTGTTGTGCTTTTGGATA</u>

<u>AGGCGGCTTCTATTGGTGGGAACTCTATAAAGGCTTCTAGTGGTATTAA</u>

<u>TGGTGCTCACACAGACACTCAACAAAATTTAAAGGTAATGGACACTCCC</u>

<u>GAATTGTTTTGAAAGATACTTTGCATTCGGCTAAAGGCAGAGGGGTTC</u>

<u>CATCACTGATGGATAAGTTGACTAAGGAATCCAAGAGTGCTATCAGGTG</u>

<u>GTTGCAAACAGAATTCGATTTGAAATTAGACCTCCTTGCGCAATTGGGC</u>

<u>GGTCACTCTGTTCCAAGGACCCATAGATCTTCTGGCAAATTACCACCAG</u>

<u>GTTTTGAAATCGTGCAAGCGTTATCAAAAAAACTAAAGGATATCTCTTC</u>

<u>CAAAGATTCCAATCTCGTGCAGATTATGCTAAACAGTGAAGTAGTGGAT</u>

<u>ATCGAGCTTGATAATCAAGGTCATGTTACTGGTGTAGTATATATGGACG</u>

<u>AGAACGGAAACCGTAAAATCATGAAATCACACCATGTCGTGTTTTGCTC</u>

<u>AGGTGGATTTGGTTACTCTAAGGAAATGTTGAAAGAGTACTCACCAAAT</u>

<u>TTGATTCACTTGCCAACTACTAATGGCAAACAGACTACAGGTGATGGTC</u>

<u>AAAAAATCCTTTCAAAGTTGGGTGCCGAATTGATTGATATGGATCAAGT</u>

<u>GCAGGTACACCCTACCGGCTTCATTGATCCAAATGACCGTGAAAATAAC</u>

<u>TGGAAGTTTTTGGCTGCAGAGGCATTGAGGGGTTTAGGCGGCATCTTAT</u>

<u>TGCATCCCACCACTGGAAGAAGATTTACAAATGAATTGAGCACCAGAGA</u>

<u>TACAGTAACCATGGAAATACAGTCTAAATGTCCGAAAAATGATAATAGA</u>

<u>GCACTTTTGGTAATGAGCGACAAAGTCTACGAGAACTATACGAATAACA</u>

<u>TAAACTTTTATATGTCCAAAAACTTAATCAAAAAAGTGTCAATCAACGA</u>

<u>TCTGATCCGACAATATGACCTACAAACTACAGCTTCTGAACTGGTGACT</u>

<u>GAACTGAAGAGTTATTCCGATGTTAATACTAAGGATACGTTTGATAGGC</u>

<u>CATTGATTATCAATGCCTTTGATAAAGATATTTCGACTGAATCAACTGT</u>

<u>TTATGTTGGGGAAGTTACACCAGTTGTTCATTTCACAATGGGTGGTGTG</u>

<u>AAAATTAATGAGAAATCTCAGGTAATTAAGAAAAATTCGGAAAGCGTTC</u>

<u>TATCTAATGGGATATTTGCTGCTGGTGAAGTTTCGGGTGGTGTTCATGG</u>

<u>AGCCAACAGATTGGGTGGATCTAGTTTGTTAGAGTGTGTTGTCTTTGGA</u>

<u>AAGACAGCTGCGGATAACATAGCAAAATTGTACTGA</u>

To overexpress OSM1-L and OSM1-S, the EFB1 promoter, represented by SEQ ID NO: 2, below, was operably-linked to the aforementioned fumarate reductase coding sequences.

(SEQ ID NO: 2)
GCAACACACGAGTATGTTGTACCTAAATCAATACCGACAGCTTTTGACA

TATTATCTGTTATTTACTTGAATTTTTGTTTCTTGTAATACTTGATTAC

TTTTCTTTTGATGTGCTTATCTTACAAATAGAGAAAATAAAACAACTTA

AGTAAGAATTGGGAAACGAAACTACAACTCAATCCCTTCTCGAAGATAC

ATCAATCCACCCCTTATATAACCTTGAAGTCCTCGAAACGATCAGCTAA

TCTAAATGGCCCCCCTTCTTTTTGGGTTCTTTCTCTCCCTTTTGCCGCC

GATGGAACGTTCTGGAAAAAGAAGAATAATTTAATTACTTTCTCAACTA

AAATCTGGAGAAAAAACGCAAATGACAGCTTCTAAACGTTCCGTGTGCT

TTCTTTCTAGAATGTTCTGGAAAGTTTACAACAATCCACAAGAACGAAA

ATGCCGTTGACAATGATGAAACCATCATCCACACACCGCGCACACGTGC

TTTATTTCTTTTTCTGAATTTTTTTTTTCCGCCATTTTCAACCAAGGAA

ATTTTTTTTCTTAGGGCTCAGAACCTGCAGGTGAAGAAGCGCTTTAGAA

ATCAAAGCACAACGTAACAATTTGTCGACAACCGAGCCTTTGAAGAAAA

AATTTTTCACATTGTCGCCTCTAAATAAATAGITTAAGGTTATCTACCC

ACTATATTTAGTTGGTTCTTTTTTTTTTCCTTCTACTCTTTATCTTTTT

ACCTCATGCTTTCTACCTTTCAGCACTGAAGAGTCCAACCGAATATATA

CACACATA

The EFB1 promoter provides about an 80-fold increase in mRNA expression of OSM1-L and OSM1-S compared to the wild-type promoter (data not shown).

The long form of the fumarate reductase polypeptide, produced from translation of the OSM1-L polynucleotide, is represented, below, by SEQ ID NO: 3. The short form of the fumarate reductase polypeptide, produced from translation of the OSM1-S polynucleotide (and likely to some level from the internal translation initiation site of the OSM1-L polynucleotide, as well), is represented, below by the underlined portion of SEQ ID NO: 3. The starting methionines are shown in bold.

(SEQ ID NO: 3)
MIRSVRRVFIYVSIFVLIIVLKRTLSGTDQTS<u>MKQPVVVIGSGLAGLIT</u>

<u>SNRLISKYRIPVVLLDKAASIGGNSIKASSGINGAHTDTQQNLKVMDTP</u>

<u>ELFLKDTLHSAKGRGVPSLMDKLTKESKSAIRWLQTEFDLKLDLLAQLG</u>

<u>GHSVPRTHRSSGKLPPGFEIVQALSKKLKDISSKDSNLVQIMLNSEVVD</u>

<u>IELDNQGHVTGVVYMDENGNRKIMKSHHVVFCSGGFGYSKEMLKEYSPN</u>

<u>LIHLPTTNGKQTTGDGQKILSKLGAELIDMDQVQVHPTGFIDPNDRENN</u>

<u>WKFLAAEALRGLGGILLHPTTGRRFTNELSTRDTVTMEIQSKCPKNDNR</u>

<u>ALLVMSDKVYENYTNNINFYMSKNLIKKVSINDLIRQYDLOTTASELVT</u>

<u>ELKSYSDVNTKDTFDRPLIINAFDKDISTESTVYVGEVTPVVHFTMGGV</u>

<u>KINEKSQVIKKNSESVLSNGIFAAGEVSGGVHGANRLGGSSLLECVVFG</u>

<u>KTAADNIAKLY*</u>

DNA fragments including the EFB1 promoter linked to OSM1-L or OSM1-S were amplified by PCR. The described sequences were flanked by 50-nt-long sequences homologous to a chromosomal locus upstream of the PAM1 locus (YDR251W) in the *S. cerevisiae* chromosome.

The PCR products were separately transformed together with plasmid pQM004 into parental cells, i.e., either (i) FERMAX™ Gold (Martrex Inc., Minnesota, USA; herein abbreviated, "FG"), a well-known fermentation yeast used in the grain ethanol industry, or (ii) FG-PKL (or simply PKL), engineered FG yeast having a heterologous phosphoketolase (PKL) pathway involving the expression of phosphoketolase (PKL), phosphotransacetylase (PTA) and acetylating acetyl dehydrogenase (AADH), as described in WO2015148272 (Miasnikov et al., supra). Plasmid pMQ004, which temporarily exists in yeast transformants, encodes the RNA-guided DNA endonuclease Cas9 and a gRNA (AGTCTCGAGAATGGCAAGCA; SEQ ID NO: 4) specific to the aforementioned target site upstream of PAM1. Both PCR products were then gap repaired in cells to form integrated EFB1 promoter-OSM1-L or EFB1 promoter-OSM1-S cassettes. upstream of PAM1 locus.

The modified yeast strains were grown in non-selective media to cure the yeast of the kanamycin resistance gene used to select transformants, resulting in modified yeast that required no growth supplements compared to the parental yeast. The integration of the cassette containing the new promoter and the coding region of OSM1 at the PAM1 site in FG, and the PKL derivative of FG, was confirmed by colony PCR, the positive strains which were used for further study.

Example 3: Ethanol Production by Yeast Overexpressing OSM1

Yeast strains overexpressing the OSM1 gene (i.e., FG-OSM1-L and FG-OSM1-S) were tested for their ability to produce ethanol compared to the FG parental yeast, which is wild-type for the OSM1 gene, in liquefact at 32° C. Liquefact having a DS of 33.5%, was prepared as generally described in Example 1. 50 g of liquefact was weighted into 100 ml vessels and inoculated with fresh overnight cultures from colonies of the modified strains or control FG strain and incubated at 32° C. Samples were harvested by centrifugation after 25 and 55 hr, filtered through 0.2 µm filters, and analyzed for glucose and ethanol content by HPLC (Agilent Technologies 1200 series) using Bio-Rad AMINEX™ HPX-87H columns at 55° C., with an isocratic flow rate of 0.6 ml/min in 0.01 N $H_2SO_4$ eluent. The results of the analyses are shown in Tables 1. Ethanol production is reported with reference to the FG strain.

TABLE 1

Analysis of fermentation broth following fermentation with yeast overexpressing OSM1

| Strain | Time (hr) | Glucose (g/L) | Ethanol (g/L) | Ethanol compared to FG |
|---|---|---|---|---|
| FG | 24 | 83.5 | 94.1 | -1- |
| FG-OSM1-S | 24 | 84.1 | 97.5 | 1.036 |
| FG-OSM1-L | 24 | 83.2 | 98.3 | 1.045 |
| FG | 55 | 0.63 | 142.9 | -1- |
| FG-OSM1-S | 55 | 0.66 | 143.8 | 1.01 |
| FG-OSM1-L | 55 | 0.65 | 143.2 | 1.00 |

Yeast overexpressing the OSM1 gene produced significantly, i.e., from 3.6% to 4.5%, more ethanol compared to the reference strain at 24 hr. Little difference was observed at the 55-hr timepoint, suggesting that overexpression of OSM1 increases the rate, but not the maximum level, of ethanol production in cells.

Example 4. Ethanol Production by Yeast Having an Alternative Ethanol-Producing Pathway and Overexpressing OSM1

Yeast strains overexpressing the OSM1 gene and further harboring a heterologous PKL pathway, i.e., strains PKL-OSM1-L and PKL-OSM1-S were additionally tested for their ability to produce ethanol compared to the parental strain, in liquefact at 32° C. Liquefact having a DS of 33.5% was generally prepared as described in Example 1. Inoculation, fermentation and analyses were performed as in Example 3. Ethanol production is reported with reference to the PKL strain is reported in Table 2.

TABLE 2

Analysis of fermentation broth following fermentation with yeast overexpressing OSM1 and harboring an exogenous PKL pathway

| Strain | Time (hr) | Glucose (g/L) | Ethanol (g/L) | Ethanol compared to PKL |
|---|---|---|---|---|
| PKL | 25 | 88.8 | 95.3 | -1- |
| PKL-OSM1-L | 25 | 86.5 | 96.9 | 1.018 |
| PKL-OSM1-S | 25 | 85.7 | 97.5 | 1.024 |
| PKL | 55 | 0.73 | 145.1 | -1- |
| PKL-OSM1-L | 55 | 0.75 | 144.7 | 0.997 |
| PKL-OSM1-S | 55 | 0.68 | 145.5 | 1.002 |

Yeast overexpressing the OSM1 gene produced significantly, i.e., about 1.8% to 2.4% more ethanol compared to the PG-PKL reference strain at 24 hr. Little difference was observed at the 55-hr timepoint, again suggesting that overexpression of OSM1 increases the rate, but not the maximum level, of ethanol production in cells.

What is claimed is:

1. A method for increasing the rate of ethanol production in yeast cells grown on a carbohydrate substrate comprising: introducing into parental yeast cells a genetic alteration that causes the modified yeast cells to produce an increased amount of fumarate reductase compared to the parental yeast cells,
   wherein the modified yeast cells have an increased rate of fermentation compared to the rate of fermentation of the parental yeast cells under equivalent fermentation conditions;
   wherein the carbohydrate substrate is substantially free of xylose; and
   wherein the fumarate reductase comprises an amino acid sequence having at least 90% sequence identity to the sequence set forth by SEQ ID NO: 3 or an amino acid sequence having at least 90% sequence identity to amino acids 33 to 501 of the sequence set forth by SEQ ID NO:3.

2. The method of claim 1, wherein the genetic alteration comprises introduction into the parental yeast cells of a nucleic acid capable of directing the expression of fumarate reductase to a level greater than that of the parental yeast cells grown under equivalent conditions.

3. The method of claim 1, wherein the genetic alteration comprises introduction of an expression cassette for expressing the fumarate reductase.

4. The method of claim 1, wherein the fumarate reductase comprises an amino acid sequence having at least 95% sequence identity to the sequence set forth by SEQ ID NO: 3.

5. The method of claim 1, wherein the fumarate reductase is an amino acid sequence having at least 95% sequence identity to amino acids 33 to 501 of the sequence set forth by SEQ ID NO: 3.

6. The method of claim 1, wherein the rate of ethanol production is measured at 24 hours into fermentation.

7. The method of claim 1, wherein the increased rate of ethanol production is not due to the metabolism of xylose.

8. The method of claim 1, wherein the modified yeast cells further comprise one or more genes of the phosphoketolase pathway.

9. The method of claim 8, wherein the genes of the phosphoketolase pathway are selected from the group consisting of phosphoketolase, phosphotransacetylase and acetylating acetyl dehydrogenase.

10. The method of claim 1, wherein the amount of increase in the expression of fumarate reductase is at least 80-fold compared to the level of expression in parental yeast cells grown under equivalent conditions, based on OSM1 mRNA expression.

11. The method of claim 1, wherein the modified yeast cells further comprise an exogenous gene encoding a carbohydrate processing enzyme.

12. The method of claim 1, wherein the modified yeast cells further comprise an alteration in the glycerol pathway and/or the acetyl-CoA pathway.

13. The method of claim 1, wherein the modified yeast cells further comprise an alternative pathway for making ethanol.

14. The method of claim 1, wherein the modified yeast cells are of a *Saccharomyces* spp.

15. The method of claim 1, wherein the fumarate reductase comprises an amino acid sequence having at least 99% sequence identity to the sequence set forth by SEQ ID NO: 3.

16. The method of claim 1, wherein the fumarate reductase is an amino acid sequence having at least 99% sequence identity to amino acids 33 to 501 of the sequence set forth by SEQ ID NO: 3.

17. The method of claim 1, wherein the fumarate reductase is the amino acid sequence set forth by SEQ ID NO: 3.

18. The method of claim 1, wherein the fumarate reductase is the amino acids 33 to 501 of the sequence set forth by SEQ ID NO: 3.

19. The method of claim 1, wherein the amount of increase in the expression of fumarate reductase is at least 60-fold compared to the level of expression in parental yeast cells grown under equivalent conditions, based on OSM1 mRNA expression.

* * * * *